（12）United States Patent　　　　　(10) Patent No.: US 8,836,947 B2
Amako et al.　　　　　　　　　　　　　　　　(45) Date of Patent: Sep. 16, 2014

(54) SAMPLE ANALYSIS ELEMENT AND DETECTING DEVICE

(71) Applicant: Seiko Epson Corporation, Tokyo (JP)

(72) Inventors: Jun Amako, Tsurugashima (JP); Mamoru Sugimoto, Chino (JP); Hideaki Koike, Chino (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 13/743,919

(22) Filed: Jan. 17, 2013

(65) Prior Publication Data

US 2013/0182258 A1　　Jul. 18, 2013

(30) Foreign Application Priority Data

Jan. 18, 2012　(JP) .................. 2012-008162

(51) Int. Cl.
*G01N 21/55*　　(2014.01)
(52) U.S. Cl.
CPC .............. G01N 21/55 (2013.01); G01N 21/554 (2013.01)
USPC ........................................................ 356/445
(58) Field of Classification Search
CPC ............................ G01N 21/55; G01N 21/554
USPC .............. 356/445, 217–319; 422/68.1, 82.05, 422/82.09, 82.11; 436/164, 171, 86, 94
See application file for complete search history.

(56) References Cited

U.S. PATENT DOCUMENTS

| | | | |
|---|---|---|---|
| 7,079,250 B2 | 7/2006 | Mukai | |
| 7,088,449 B1 * | 8/2006 | Brongersma | 356/445 |
| 7,351,588 B2 | 4/2008 | Poponin | |
| 7,399,445 B2 | 7/2008 | Kuroda et al. | |
| 7,483,130 B2 * | 1/2009 | Baumberg et al. | 356/301 |
| 7,639,355 B2 | 12/2009 | Fattal et al. | |

(Continued)

FOREIGN PATENT DOCUMENTS

| | | |
|---|---|---|
| EP | 2 372 348 | 10/2011 |
| JP | 2000-356587 | 12/2000 |

(Continued)

OTHER PUBLICATIONS

Jean Cesario, "Electromagnetic Coupling Between a Metal Nanoparticle Grating and a Metallic Surface", Optical Society of America, Optics Letters, vol. 30, No. 24, Dec. 15, 2005, pp. 3404-3406.

(Continued)

*Primary Examiner* — Sang Nguyen
(74) *Attorney, Agent, or Firm* — Harness, Dickey & Pierce, P.L.C.

(57) ABSTRACT

A plurality of metallic nano-body groups that includes metallic nano-bodies which are a size smaller than the wavelength of incident light and are dispersed on a dielectric surface is arranged in one direction at a pitch that resonates with the incident light. A long piece extends on the dielectric surface between adjacent metallic nano-body groups. The long piece is formed of a material having no free electron that performs resonance oscillation with the incident light. Localized surface plasmon resonance occurs in the metallic nano-body by the action of the incident light. Propagating surface plasmon resonance occurs by the action of the pitch. The propagating surface plasmon resonance is combined with the localized surface plasmon resonance. A so-called hybrid mode is established. The long piece is helpful in the establishment of the pitch.

8 Claims, 10 Drawing Sheets

(56) References Cited

U.S. PATENT DOCUMENTS

| | | |
|---|---|---|
| 7,733,491 B2 | 6/2010 | Kuroda et al. |
| 7,768,640 B2 * | 8/2010 | Cunningham et al. ........ 356/317 |
| 8,085,405 B2 | 12/2011 | Ogawa |
| 8,093,065 B2 | 1/2012 | Poponin |
| 8,107,071 B2 * | 1/2012 | Kimura ........................ 356/318 |
| 8,247,216 B2 * | 8/2012 | Zaccarin et al. ........... 435/283.1 |
| 2006/0194344 A1 | 8/2006 | Saito |
| 2008/0198376 A1 | 8/2008 | Poponin |
| 2009/0109422 A1 * | 4/2009 | Handa et al. .................... 356/39 |
| 2010/0167946 A1 * | 7/2010 | Shaw et al. ........................ 506/9 |
| 2010/0178713 A1 | 7/2010 | Nishiuma et al. |
| 2011/0114859 A1 | 5/2011 | Amako et al. |
| 2011/0116088 A1 | 5/2011 | Amako et al. |
| 2012/0019828 A1 * | 1/2012 | McCaffrey et al. ........... 356/432 |
| 2012/0107958 A1 | 5/2012 | Poponin |
| 2012/0257204 A1 * | 10/2012 | Walters ........................ 356/445 |

FOREIGN PATENT DOCUMENTS

| | | |
|---|---|---|
| JP | 2003-268592 | 9/2003 |
| JP | 2003-270132 | 9/2003 |
| JP | 2006-208057 | 8/2006 |
| JP | 2007-218900 | 8/2007 |
| JP | 2007-240361 | 9/2007 |
| JP | 2007-248284 | 9/2007 |
| JP | 2007-303973 | 11/2007 |
| JP | 2008-292425 | 12/2008 |
| JP | 2009-222401 | 10/2009 |
| JP | 2011-128133 | 6/2011 |
| JP | 2011-128135 | 6/2011 |
| JP | 2011-141264 | 7/2011 |
| JP | 2011-141265 | 7/2011 |

OTHER PUBLICATIONS

N. Felidj et al., "Enhanced Substrate-Induced Coupling in Two-Dimensional Gold Nanoparticle Arrays", Physical Review B 66, The American Physical Society, 2002, pp. 245407-1 through 245407-7.

Y. Chu et al., "Experimental Study of the Interaction Between Localized and Propagating Surface Plasmons", Optical Society of America, Optics Letters, vol. 34, No. 3, Feb. 1, 2009, pp. 244-246.

L. Du et al., "Localized Surface Plasmons, Surface Plasmon Polaritons, and Their Coupling in 2D Metallic Array for SERS", Optical Society of America, Optics Express, vol. 18, No. 3, Feb. 1, 2010, pp. 1959-1965.

M. Inoue et al., "Surface Enhanced Raman Scattering by Metal Spheres, I. Cluster Effect", Journal of the Physical Society of Japan, vol. 52, No. 11, Nov. 1983, pp. 3853-3864.

* cited by examiner

SAMPLE ANALYSIS ELEMENT AND DETECTING DEVICE

BACKGROUND

1. Technical Field

The present invention relates to a sample analysis element, a detecting device, and the like that are provided with a metallic nano-body such as a metallic nanoparticle or a metallic nano-projection.

2. Related Art

A sample analysis element using localized surface plasmon resonance (LSPR) is known. Such a sample analysis element is provided with metallic nano-bodies, that is, metallic nanoparticles which are dispersed on, for example, a dielectric surface. The metallic nanoparticle is formed sufficiently smaller than the wavelength of excitation light, for example. If the metallic nanoparticle is irradiated with the excitation light, an electric dipole is induced on the particle and an electric field is generated around the particle. As a result, a strong local electric field due to the interaction between the electric dipoles is generated between the metallic nanoparticle and the metallic nanoparticle. Such a site is called a hot spot.

In Yizhuo Chu et al, "Experimental study of the interaction between localized and propagating surface plasmons", OPTICS LETTERS, U.S.A. Feb. 1, 2009, Vol. 34, No. 3, p. 244-246, the metallic nanoparticles are disposed in a lattice form at a predetermined pitch. If the size of the pitch is set to be a specific numerical value, propagating surface plasmon (PSP) based on an evanescent wave occurring. The propagating surface plasmon is combined with the localized surface plasmon, and thus a so-called hybrid mode is established. The localized surface plasmon resonance is further enhanced through the combination, and thus, near-field light that is generated on the surface of the metallic nanoparticle is further intensified.

JP-A-2009-222401 is an example of related art.

The sample analysis element described above can be used in a target substance detection device. However, as disclosed in Yizhuo Chu et al, "Experimental study of the interaction between localized and propagating surface plasmons", OPTICS LETTERS, U.S.A. Feb. 1, 2009, Vol. 34, No. 3, p. 244-246, since the wavelength of the evanescent wave that causes the propagating surface plasmon resonance is determined by an array pitch of the metallic nanoparticle, the surface density of the hot spot on the dielectric surface is reduced. For this reason, establishment to detect target substance at the hot spot becomes very low, and thus it is not possible to realize a high sensitive sample analysis element and a detecting device.

SUMMARY

An advantage of some aspects of the invention is that a sample analysis element and a detecting device can be provided in which it is possible to combine the propagating surface plasmon resonance with the localized surface plasmon resonance while increasing the surface density of a hot spot.

(1) An aspect of the invention is directed to a sample analysis element including: a dielectric surface; a plurality of metallic nano-body groups that includes metallic nano-bodies each having a size smaller than the wavelength of incident light and dispersed on the dielectric surface and that is arranged in at least one direction at a pitch that resonates with the incident light; and a long piece that is formed of a material having no free electron that performs resonance oscillation with the incident light and extends on the dielectric surface between adjacent metallic nano-body groups.

Localized surface plasmon resonance occurs in the metallic nano-body by the action of the incident light. Propagating surface plasmon resonance based on an evanescent wave occurs by the action of the pitch of the metallic nano-body group. The propagating surface plasmon is combined with the localized surface plasmon, and thus a so-called hybrid mode is established. In this way, the localized surface plasmon resonance is enhanced by the propagating surface plasmon resonance, and thus, near-field light is intensified on the surface of the metallic nano-body. A so-called hot spot is formed. In addition, since a plurality of metallic nano-bodies is disposed in each metallic nano-body group, compared to a case where the metallic nano-body is disposed at the pitch that resonates with incident light, the surface density of the metallic nano-body is increased. Therefore, the surface density of the hot spot is increased. In addition, since a space between the metallic nano-body groups is occupied by a material having no free electron that performs resonance oscillation, the pitch of the metallic nano-body group can be reliably established. The generation of the propagating surface plasmon resonance can be reliably secured.

(2) In the sample analysis element according to the above aspect, the height of the long piece may be higher than the height of the metallic nano-body. According to such a structure, even if the metallic nano-body is cut in the manufacturing process, a space between the metallic nano-body groups can be reliably occupied by the material having no free electron that performs resonance oscillation. Therefore, the pitch of the metallic nano-body group can be reliably established. The generation of the propagating surface plasmon resonance can be reliably secured.

(3) In the sample analysis element according to the above aspect, the metallic nano-body group may be subdivided into metallic nano-body groups that are arranged at the pitch that resonates with the incident light, in a second direction intersecting a first direction in a case where one direction is set to be the first direction, and a second long piece may extend on the dielectric surface between the subdivided metallic nano-body groups. In such a sample analysis element, the pitches can be set in two directions intersecting each other. As a result, the propagating surface plasmon resonance can be established in two directions. As a result, incident light can have a plurality of polarization planes. The incident light can have circularly-polarized light.

(4) In the sample analysis element according to the above aspect, the metallic nano-body may be an island-shaped metallic nanoparticle. The long piece can be formed on the dielectric surface in advance in the formation of the metallic nano-body in the manufacturing process of the sample analysis element. Therefore, the metallic nanoparticle can be formed according to the aggregation of thin films in between the long pieces. As a result, the pitch of the metallic nano-body group can be reliably established. The generation of the propagating surface plasmon resonance can be reliably secured.

(5) The sample analysis element as described above can be used in a detecting device. The detecting device may include, for example, a light source that emits light toward the metallic nano-body group of the sample analysis element, and a photodetector that detects the light that is emitted from the metallic nano-body group according to the irradiation of the light.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, an embodiment of the invention will be described with reference to the accompanying drawings. In addition, the embodiment that is described below does not unduly limit the contents of the invention stated in the appended claims, and all of the configurations that are described in this embodiment are not necessarily essential as solving means of the invention.

1. Structure of Sample Analysis Element

Figure 1:
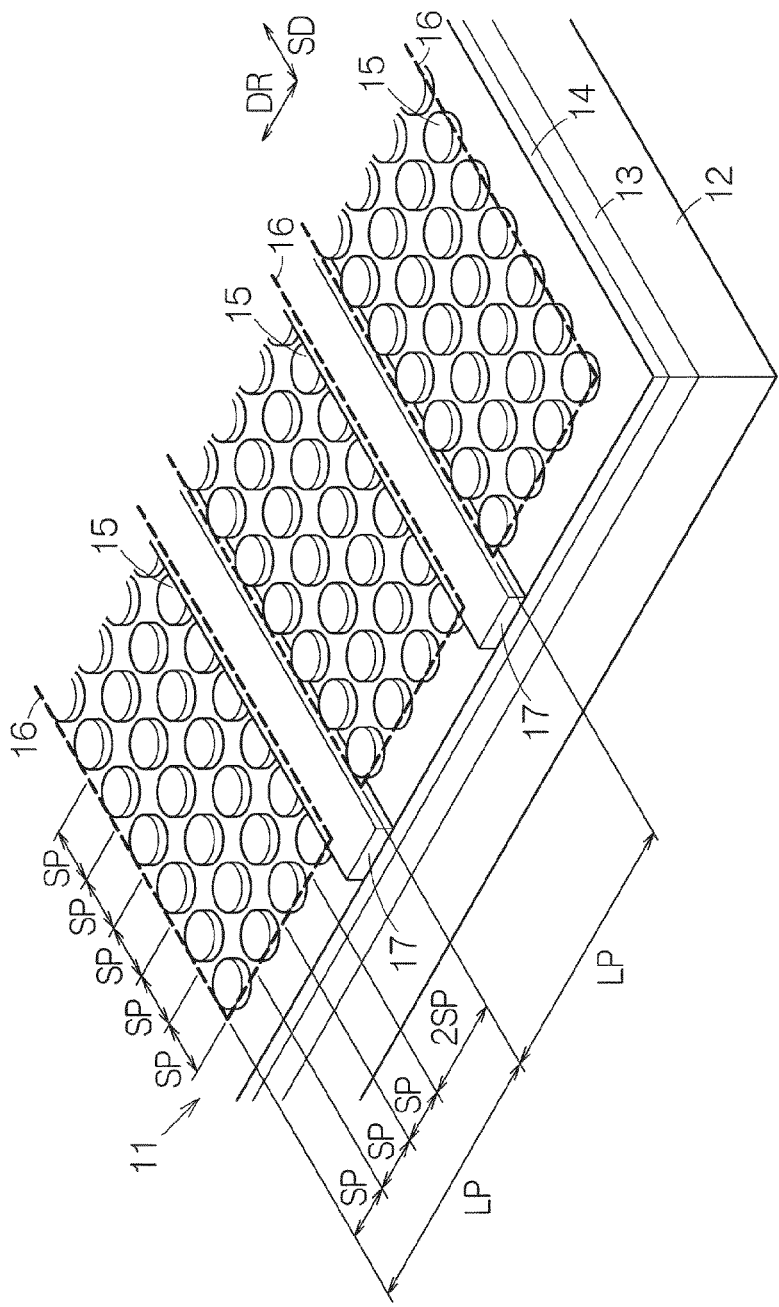
FIG. 1 is a perspective view schematically showing a sample analysis element according to an embodiment of the invention.

FIG. 1 schematically shows a sample analysis element 11 according to an embodiment of the invention. The sample analysis element 11 includes a substrate 12. The substrate 12 is formed of, for example, a dielectric. As for the dielectric, for example, silicon oxide ($SiO_2$) or glass can be used.

A metal film 13 is formed on the surface of the substrate 12. The metal film 13 is formed of metal. The metal film 13 can be formed of, for example, gold. The metal film 13 can be formed, for example, on the surface of the substrate 12 in a continuous way over the entire surface. The film thickness of the metal film 13 can be set to be greater than or equal to about 100 nm, for example.

A dielectric film (a dielectric) 14 is formed on the surface of the metal film 13. The dielectric film 14 is formed of a dielectric. The dielectric film 14 can be formed of an oxide film such as $SiO_2$, for example. The dielectric film 14 can be formed, for example, on the surface of the metal film 13 in a continuous way over the entire surface. The film thickness of the dielectric film 14 can be set to be about 40 nm, for example.

A metallic nano-projection (a metallic nano-body) 15 is formed on the surface of the dielectric film 14. The metallic nano-projections 15 are dispersed on the surface of the dielectric film 14. The metallic nano-projection 15 is formed of a metal material. The metallic nano-projection 15 can be formed of, for example, silver. In addition, gold or aluminum may also be used to form the metallic nano-projection 15. Each metallic nano-projection 15 is formed in a cylindrical column. The diameter of the circular cross-section can be set to be in a range of 10 nm to 100 nm, for example. The height (from the surface of the dielectric film) of the cylindrical column can be set to be in a range of 5 nm to 50 nm, for example. The size of the cylindrical column is set to be sufficiently smaller than the wavelength of incident light that is assumed. The metallic nano-projection 15 may also be formed in a rectangular column or other three-dimensional shapes. In this case, the horizontal cross-section of the rectangular column may also be formed in a square, a rectangle, or other polygonal shapes.

The metallic nano-projections 15 form a metallic nano-projection group (a metallic nano-body group) 16. The metallic nano-projection groups 16 are arranged at a predetermined long pitch LP in a first direction (one direction) DR. The size of the long pitch LP is set according to the wavenumber of an evanescent wave, as will be described later. A plurality of long pieces 17 is disposed between the metallic nano-projection groups 16. That is, the long pieces 17 are disposed at the long pitch LP in the first direction DR. The long pieces 17 extend parallel in a second direction SD. Each first long piece 17 can linearly extend. Each first long piece 17 can continuously extend from an edge to an edge of the contour of the dielectric film 14.

The metallic nano-projections 15 are disposed at a short pitch SP in the first direction DR in each metallic nano-projection group 16. At the same time, the metallic nano-projections 15 are disposed at the short pitch SP in the second direction SD in each metallic nano-projection group 16. Therefore, the plurality of metallic nano-projections 15 is disposed in a lattice form in at the short pitch SP in each metallic nano-projection group 16. The short pitch SP is set to be smaller than at least the long pitch LP. In the metallic nano-projection group 16, the gap between adjacent metallic nano-projections 15 is set to be smaller than the gap between adjacent metallic nano-projection groups 16. Here, the gap between the metallic nano-projection groups 16 is set to be larger than the short pitch SP.

Figure 2:
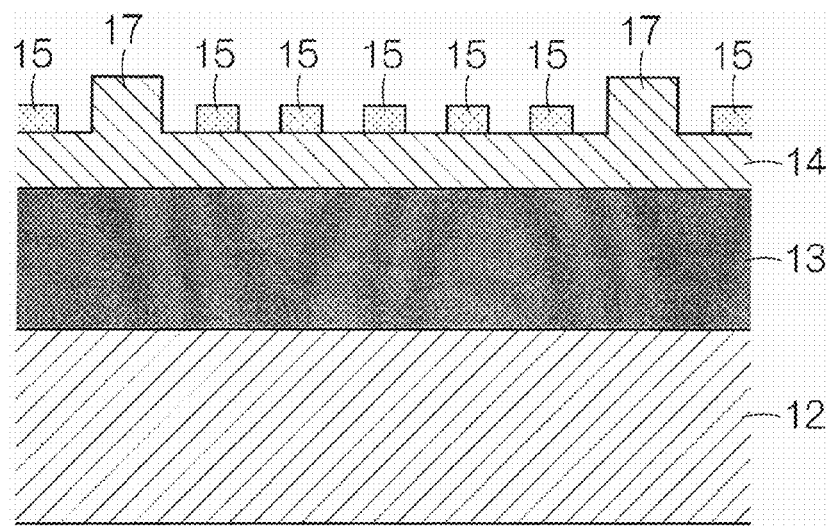
FIG. 2 is an enlarged vertical cross-sectional view of the sample analysis element.

As shown in FIG. 2, the long piece 17 extends on the surface of the dielectric film 14. The height of the long piece is set to be higher than the height of the metallic nano-projection 15. As a result, in a space that is sandwiched between an imaginary plane that includes the bottom surfaces of the metallic nano-projections 15 and an imaginary plane that includes the top surfaces of the metallic nano-projections 15, a gap between adjacent metallic nano-projection group 16 is filled with a material of the long piece 17. The metallic nano-projection groups 16 are divided by the material of the long piece 17.

The long piece 17 is formed of a material having no free electron that performs resonance oscillation with incident light. As such a material, a dielectric such as an oxide, for example, can be used. Here, the long piece is formed of silicon oxide ($SiO_2$).

Figure 3:
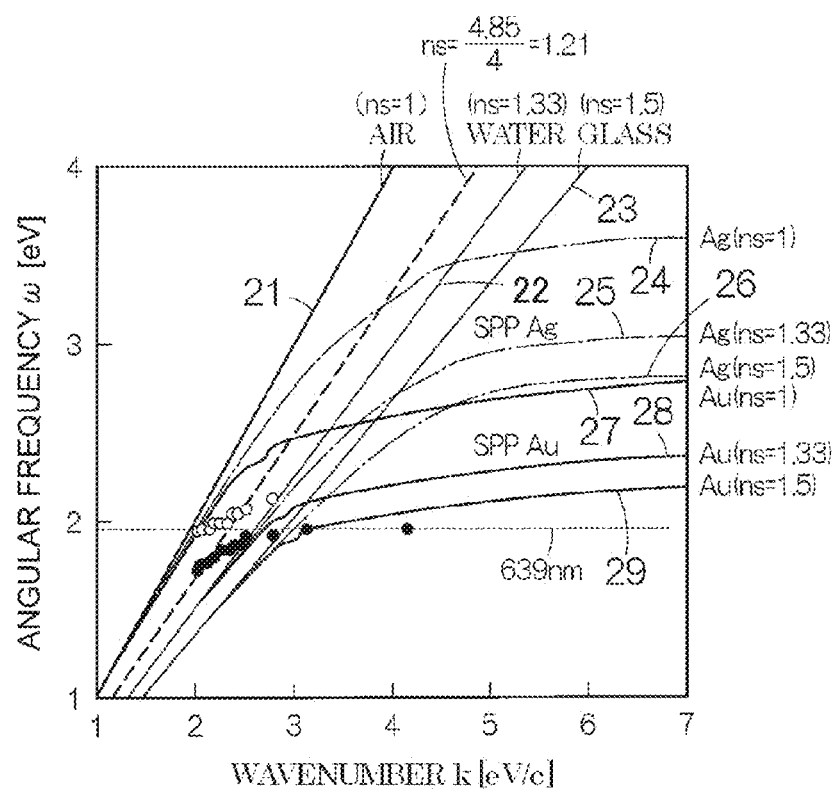
FIG. 3 is a graph showing dispersion relation.

FIG. 3 shows dispersion relation. A wavenumber k is specified according to the long pitch LP. Straight lines 21, 22, and 23 respectively show the dispersion relations of air (ns=1.0), water (ns=1.33), and glass (ns=1.5). These dispersion relations show a proportional relation. Three curved lines 24, 25, and 26 show the dispersion relations of the propagating surface plasmon resonance of silver Ag for each refractive index (ns=1.0, 1.33, and 1.5). In addition, three curved lines 27, 28, and 29 show the dispersion relations of the propagating surface plasmon resonance of gold Au for each refractive index (ns=1.0, 1.33, and 1.5). A straight line parallel to an x axis (a wavenumber) shows the angular frequency (=1.94 eV) (wavelength=639 nm) of the localized surface plasmon resonance of the metallic nano-projection 15. A white plot shows the angular frequency of incident light that forms a primary peak (an extreme value) of electric field intensity at the metallic nano-projection 15 for each long pitch LP. A black plot shows the angular frequency of incident light that forms a secondary peak of electric field intensity at the metallic nano-projection 15 for each long pitch LP. Preferably, the long pitch LP is given by the following expression.

$$LP = \lambda \cdot \mathrm{Re}\left[\sqrt{1 + \frac{1}{\varepsilon}}\right]$$

Here, λ represents the wavelength of localized surface plasmon resonance, ∈ represents the complex permittivity of the metal film 13, and Re[ ] represents a real part.

In the sample analysis element 11, if the planarization plane of incident light is fitted to an x-axis direction and a y-axis direction, the propagating surface plasmon resonance (PSPR) based on an evanescent wave occurs according to the setting of the long pitch LP. The propagating surface plasmon is combined with the localized surface plasmon (LSP) of the metallic nano-projection 15, and thus a so-called hybrid mode is established. In this way, the localized surface plasmon resonance is enhanced by the propagating surface plasmon resonance, and thus, near-field light is intensified on the surface of the metallic nano-projection 15. A so-called hot spot is formed. In addition, since the gap between the metallic nano-projections 15 is set to be the short pitch SP smaller than the long pitch LP in each metallic nano-projection group 16, compared to a case where the gap between the metallic nano-projections 15 is set to be the long pitch LP, the surface density of the metallic nano-projection 15 is increased. The surface density of the hot spot is increased. In addition, since a space between the metallic nano-projection groups 16 is occupied by the material having no free electron that performs resonance oscillation with incident light, that is, a dielectric material, the long pitch LP of the metallic nano-projection group 16 can be reliably established.

2. Verification of Electric Field Intensity

Figure 4A:
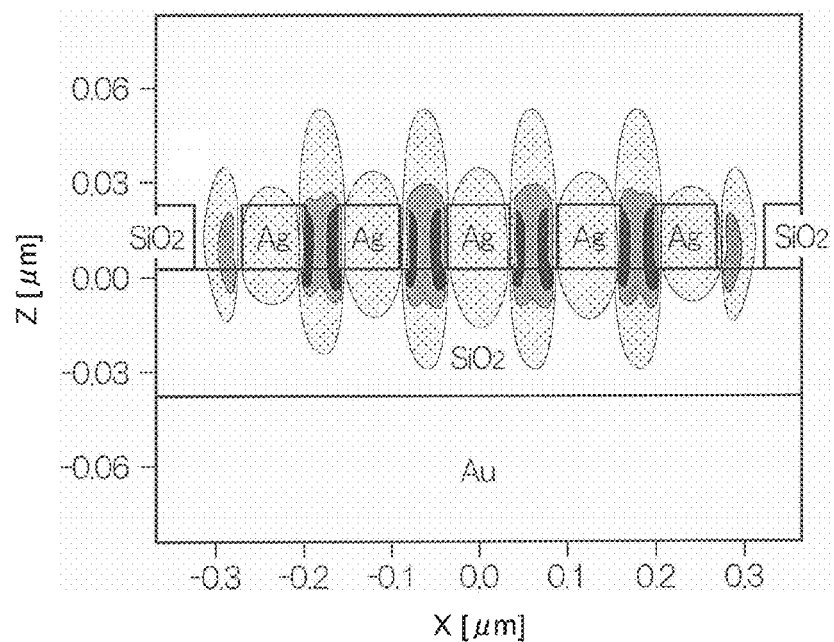
FIGS. 4A and 4B are diagrams equivalent to a vertical cross-section, that specify the concentration of a component in an x-axis direction of an electric field and the concentration of a component in a z-axis direction of the electric field in a simulation model.
Figure 4B:
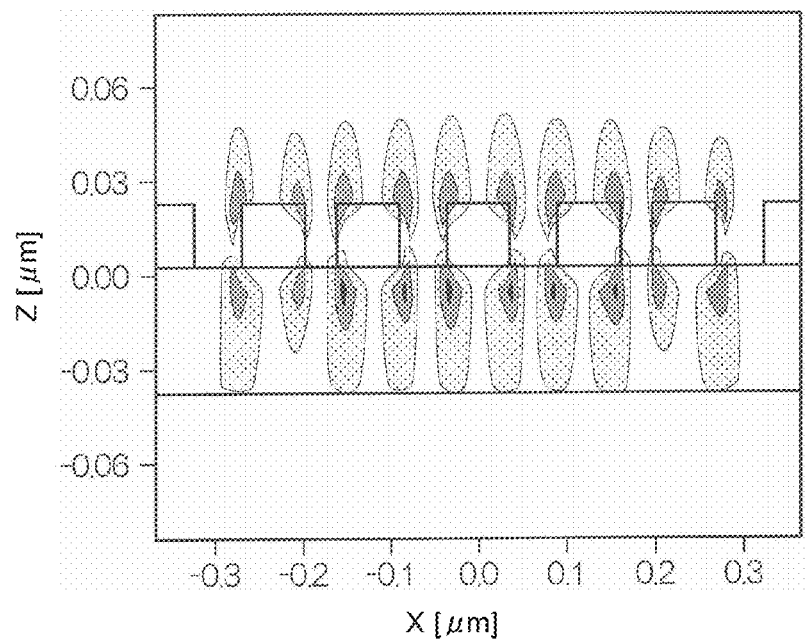

The inventor verified the electric field intensity of the sample analysis element 11. In the verification, simulation software of a FDTD (Finite-Difference Time-Domain) method was used. In the use of the simulation software, the inventor constructed a simulation model on the basis of a Yee Cell. As shown in FIGS. 4A and 4B, in the simulation model, the dielectric film 14 was laminated on the metal film 13. The material of the metal film 13 was set to be gold. The film thickness thereof was set to be 100 nm. The material of the dielectric film 14 was set to be $SiO_2$. The film thickness thereof was set to be 40 nm. The long pieces 17 were disposed at the long pitch LP of 720 nm on the dielectric film 14. The material of the long piece 17 was set to be $SiO_2$. The height (from the surface of the dielectric film 14) of the long piece 17 was set to be 20 nm. Five metallic nano-projections 15 were arranged on the dielectric film 14 between the long pieces 17. The short pitch SP was set to be 120 nm. The material of the metallic nano-projection 15 was set to be silver. The metallic nano-projection 15 was formed in the form of a circular column. The diameter of the circular cross-section was set to be 80 nm. The height (from the surface of the dielectric film) of the metallic nano-projection 15 was set to be 20 nm.

The inventor calculated electric field intensity on the basis of the prepared simulation model. In the calculation, incident light that is linearly-polarized light was set. A polarization plane was fitted to the x-axis direction of the simulation model. The wavelength of the incident light was set to be 700 nm. A peripheral refractive index ns was set to 1. The incident light was set to be vertically incident. As shown in FIG. 4A, it was observed that the component in the x-axis direction of an electric field was intensified between adjacent metallic nano-projections 15. At the same time, as shown in FIG. 4B, it was observed that the components in the z-axis direction of electric fields were concentrated on edges of the upper surface and edges of the bottom surface of the metallic nano-projection 15 between adjacent metallic nano-projections 15.

Figure 5A:
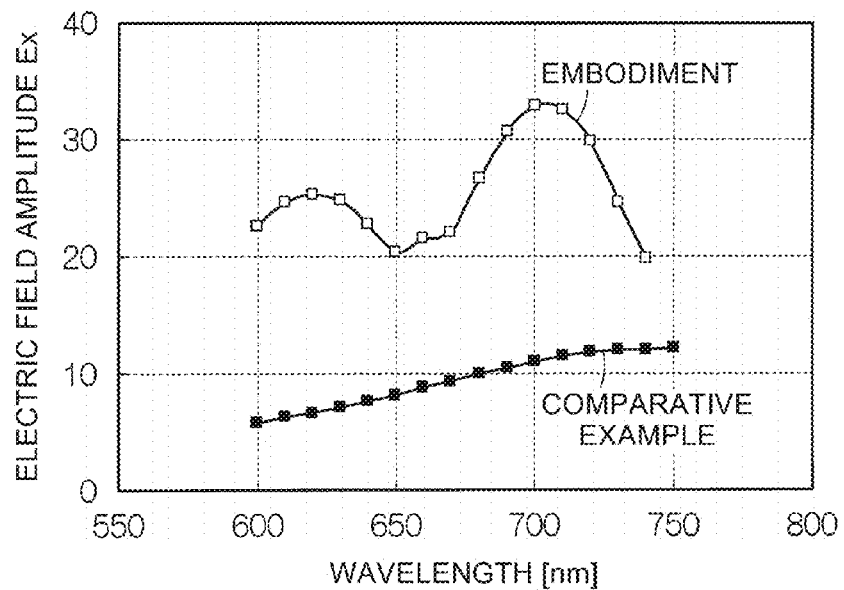
FIGS. 5A and 5B are graphs showing the frequency characteristic of the component in the x-axis direction of the electric field and the frequency characteristic of the component in the z-axis direction of the electric field.
Figure 5B:
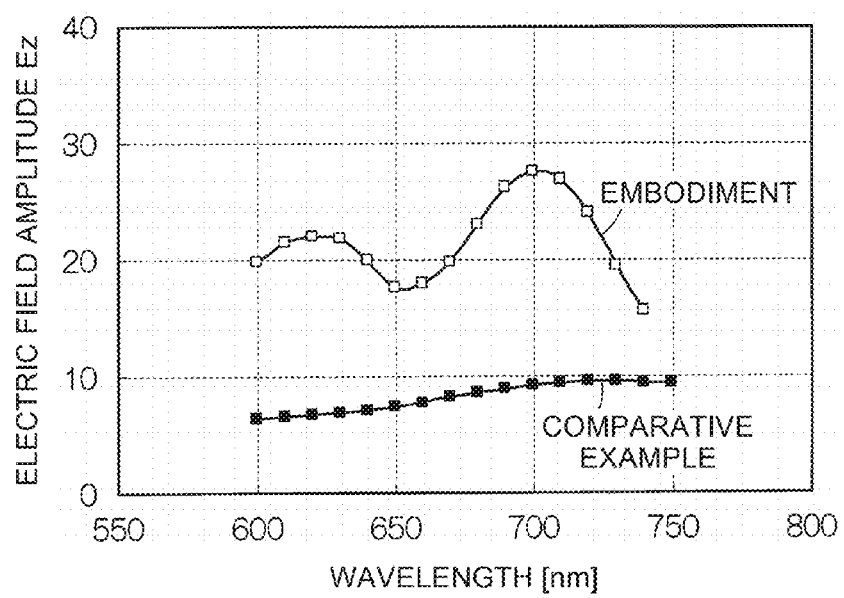

The inventor calculated electric field intensity on the basis of the above-described simulation model while changing the wavelength of incident light. In the calculation, the inventor prepared a simulation model (hereinafter referred to as a "comparative example") related to a comparative example. In the comparative example, the long piece 17 was omitted. The metallic nano-projections 15 were simply arranged in the x-axis direction at the short pitch SP of 120 nm. As shown in FIGS. 5A and 5B, it was observed that in the simulation model related to this embodiment, compared to the comparative example, electric field intensity was enhanced up to about three times at a maximum.

3. Method of Manufacturing Sample Analysis Element

Figure 6:
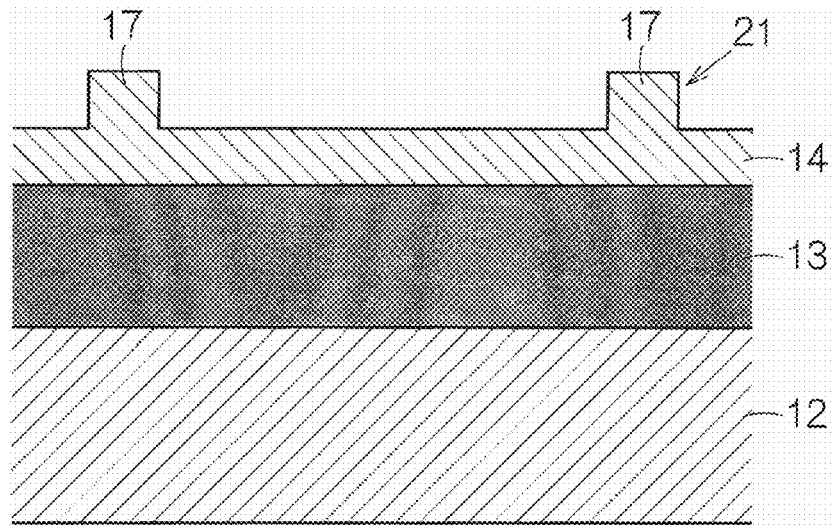
FIG. 6 is a vertical cross-sectional view showing the manufacturing process of the sample analysis element and schematically showing a metal film and a dielectric film which are laminated on a substrate.

Next, a method of manufacturing the sample analysis element 11 will be briefly described. As shown in FIG. 6, the metal film 13 is formed on the surface of the substrate 12. The metal film 13 is formed of, for example, gold. In the formation, for example, a sputtering method is used. It is favorable if the metal film 13 is formed all over on the surface of the substrate 12. The film thickness of the metal film 13 can be set to be about 100 nm, for example. The substrate 12 can be formed of, for example, $SiO_2$.

A dielectric film 21 is formed on the surface of the metal film 13. In the formation, a sputtering method can be likewise used. The dielectric film 21 is formed of, for example, $SiO_2$. It is favorable if the dielectric film 21 is formed all over on the surface of the substrate 12. Glass imprint is performed on the dielectric film 21. As a result, the dielectric film 21 is shaped into the dielectric film 14 and the long piece 17. The film thickness of the dielectric film 14 can be set to be about 40 nm, for example. The height of the long piece 17 can be set to be 40 nm, for example.

Figure 7:
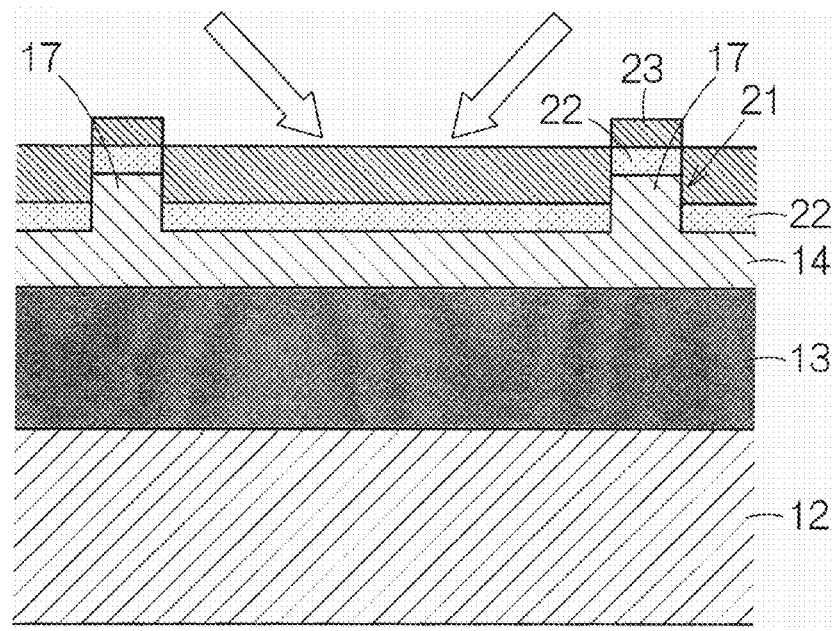
FIG. 7 is a vertical cross-sectional view showing the manufacturing process of the sample analysis element and schematically showing a material film and a resist film which are laminated on the dielectric film.

Subsequently, as shown in FIG. 7, a material film 22 made of metal is formed on the surface of the dielectric film 21. In the formation, a sputtering method can be likewise used. The material film 22 is formed of, for example, silver. It is favorable if the material film 22 is formed all over on the surface of the substrate 12. The film thickness of the material film 22 can be set to be about 20 nm, for example.

Figure 8:
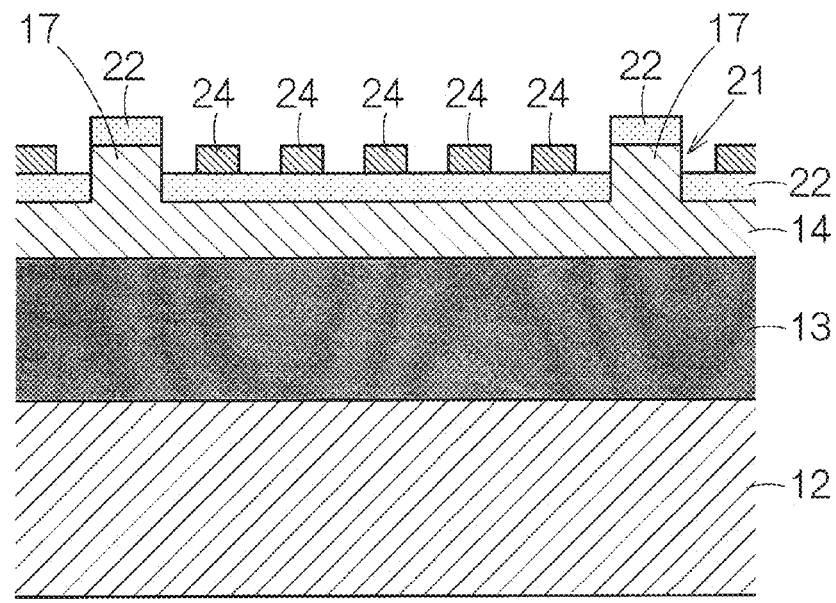
FIG. 8 is a vertical cross-sectional view showing the manufacturing process of the sample analysis element and schematically showing a resist pattern which is formed on the material film.

A resist film 23 is formed on the surface of the material film 22. In the formation, the resist film 23 can be spin-coated. The film thickness of the resist film 23 can be set to be about 20 nm, for example. The resist film 23 is exposed and developed according to a predetermined pattern. In the exposure, for example, laser interference exposure can be used. As a result, as shown in FIG. 8, resist patterns 24 modeled the metallic nano-projections 15 are formed on the material film 22 in a space that is sandwiched between the long pieces 17. The resist film 23 on the long piece 17 is removed. It is favorable if an exposing condition of the resist film 23 is appropriately set in such removal.

Figure 9:
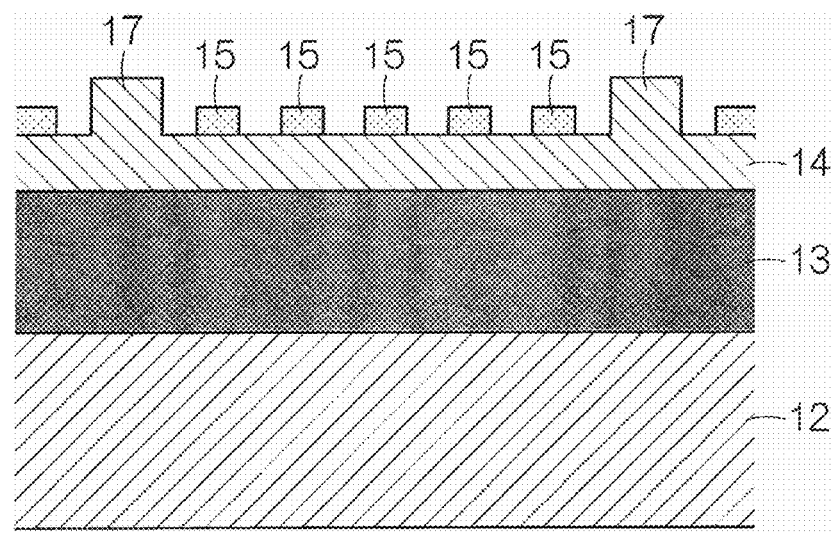
FIG. 9 is a vertical cross-sectional view showing the manufacturing process of the sample analysis element and schematically showing a metallic nano-projection cut out of the material film.

Thereafter, for example, etching treatment is performed on the material film 22. The material film 22 is selectively removed by the action of the resist pattern 24. The material film 22 is scraped off around the contour of the resist pattern 24. As a result, as shown in FIG. 9, the metallic nano-projections 15 are formed on the surface of the dielectric film 14 between the long pieces 17. At this time, since the height of the long piece 17 is set to be larger than the height of the metallic nano-projection 15, even if the long piece 17 is scraped off when the metallic nano-projection 15 is cut from the material film 22, a space between the metallic nano-projection groups 16 can be reliably occupied by the long piece 17. Therefore, the long pitch LP of the metallic nano-projection group 16 can be reliably established. The generation of the propagating surface plasmon resonance can be reliably secured.

4. Detecting Device

Figure 10:
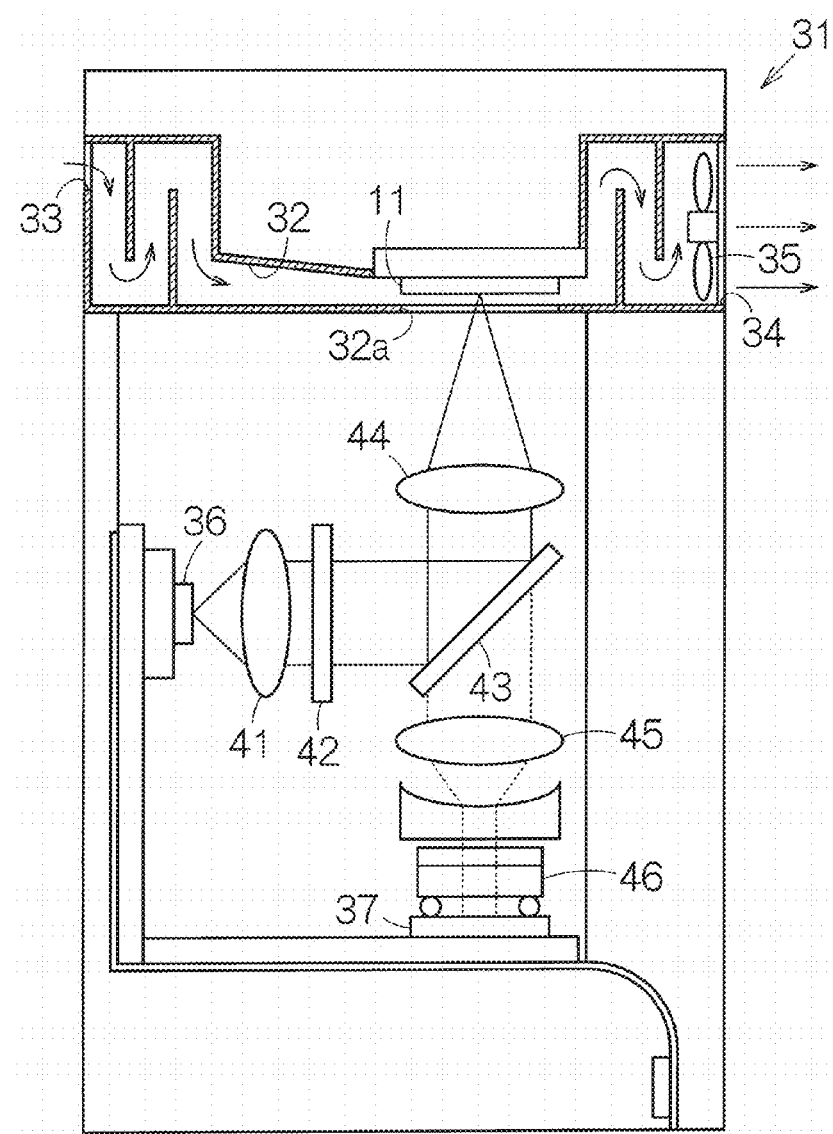
FIG. 10 is a schematic diagram schematically showing a detecting device according to an embodiment of the invention.

FIG. 10 schematically shows a detecting device 31 according to an embodiment of the invention. The detecting device 31 uses surface-enhanced Raman scattering (SERS). The detecting device 31 can detect target substances such as an adenovirus, a rhinovirus, a HIV virus, or an influenza virus, for example, on the basis of the surface-enhanced Raman scattering. The sample analysis element 11 described above, that is, a sensor chip is incorporated into the detecting device 31. In the incorporation, a transport path 32 is partitioned in the detecting device 31. A carrying-in port 33 and a discharge port 34 are formed in the transport path 32. The transport path 32 is hermetically sealed between the carrying-in port 33 and the discharge port 34. A blower fan 35 is installed in the transport path 32. The blower fan 35 generates an air current toward the discharge port 34 from the carrying-in port 33. A sample (=a mass of air) is entrained by the air current, thereby moving the transport path 32 from the carrying-in port 33 to the discharge port 34. The sample analysis element 11 described above is installed in the transport path 32.

A light source 36 is incorporated into the detecting device 31. As the light source 36, for example, a laser light source that emits laser light can be used. The light source 36 emits light, for example, at a specific wavelength.

A photodetector 37 is incorporated into the detecting device 31. As the photodetector 37, for example, a light-receiving element can be used. The light-receiving element can detect, for example, the intensity of light. The light-receiving element can output a detection current according to, for example, the intensity of light. Therefore, the intensity of light can be specified according to the magnitude of an electric current that is output from the light-receiving element.

An optical system is constructed between the light source 36 and the sample analysis element 11 and between the sample analysis element 11 and the photodetector 37. The optical system 38 forms an optical path between the light source 36 and the sample analysis element 11, and at the same time, forms an optical path between the sample analysis element 11 and the photodetector 37. The light of the light source 36 is led to the sample analysis element 11 by the action of the optical system. The reflected light of the sample analysis element 11 is led to the photodetector 37 by the action of the optical system.

The optical system includes a collimator lens 41, a polarization control element 42, a dichroic mirror 43, an objective lens 44, a condensing lens 45, and an etalon 46. The dichroic mirror 43 is disposed, for example, between the sample analysis element 11 and the photodetector 37. The objective lens 44 is disposed between the dichroic mirror 43 and the sample analysis element 11. Light passes through a transmission window 32a of the transport path 32 between the sample analysis element 11 and the objective lens 44. The transmission window 32a is blocked by, for example, a transmission material. The transmission material allows the transmission of the light from the light source 36. The condensing lens 45 and the etalon 46 are disposed between the dichroic mirror 43 and the photodetector 37. The optical axes of the objective lens 44 and the condensing lens 45 are fitted coaxially. The optical axis of the light source 36 is perpendicular to the optical axes of the objective lens 44 and the condensing lens 45. The surface of the dichroic mirror 43 intersects these optical axes at an angle of 45 degrees. The collimator lens 41 and the polarization control element 42 are disposed between the dichroic mirror 43 and the light source 36. In this way, the collimator lens 41 faces the light source 36. The optical axis of the collimator lens 41 is coaxially fitted to the optical axis of the light source 36.

The light that is emitted from the light source 36 is converted into parallel light by the collimator lens 41. The polarization control element 42 converts the light into linearly-polarized light. The linearly-polarized light is reflected by the dichroic mirror 43. The reflected light is condensed by the objective lens 44 and irradiated to the sample analysis element 11. At this time, the light can be incident in a vertical direction perpendicular to the surface of the substrate 12. A so-called vertical incidence can be established. The polarization plane of the light is fitted to the x-axis direction of the sample analysis element 11. The localized surface plasmon resonance occurs in the metallic nano-projection 15 by the action of the light irradiated. At the same time, the propagating surface plasmon resonance based on the evanescent wave occurs. The propagating surface plasmon is combined with the localized surface plasmon (LSPR) of the metallic nano-projection 15. Near-field light is intensified on the surface of the metallic nano-projection 15. A so-called hot spot is formed.

At this time, if the target substance is stuck to the metallic nano-projection 15 by the hot spot, Rayleigh-scattering light and Raman scattering light are generated from the target substance. A so-called surface-enhanced Raman scattering is achieved. As a result, the light is emitted toward the objective lens 44 in a spectrum according to the type of the target substance.

The light that is emitted from the sample analysis element 11 in this manner is converted into parallel light by the objective lens 44 and passes through the dichroic mirror 43. Thereafter, the light is condensed by the condensing lens 45. The condensed light is incident on the etalon 46. The etalon 46 disperses the Raman scattering light. In this way, the photodetector 37 detects the intensity of the light for each specific wavelength. As a result, the target substance can be detected according to the spectrum of the light. It is favorable if the spectrum of the target substance is measured in advance and stored in the detecting device 31. The detected spectrum is compared with the spectrum measured in advance.

5. Modification Examples of Sample Analysis Element

Figure 11:
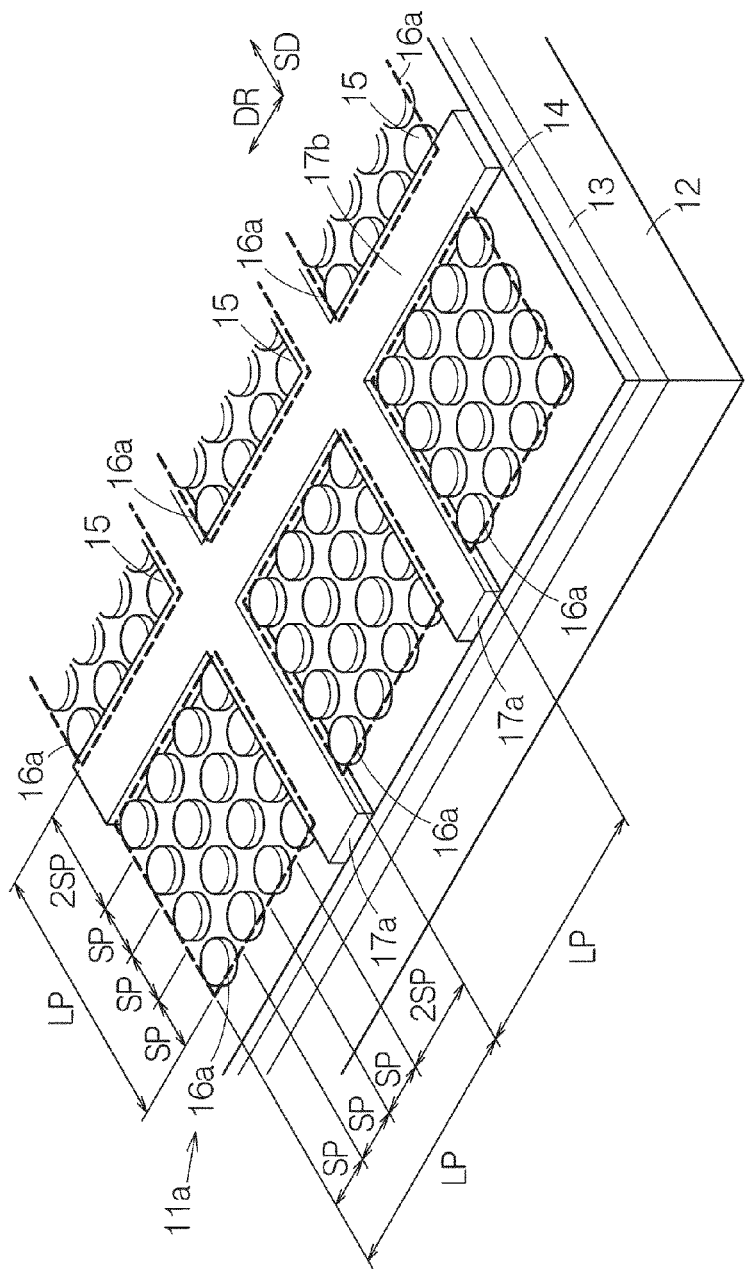
FIG. 11 is a perspective view schematically showing a sample analysis element according to a modification example.

FIG. 11 schematically shows a sample analysis element 11a according to a modification example. In the sample analysis element 11a, a metallic nano-projection group 16a is subdivided in the second direction SD as well as the first direction DR described above. That is, the metallic nano-projection groups 16a are arranged at the predetermined long pitch LP in the first direction DR and at the same time, arranged at the predetermined long pitch LP in the second direction SD. In the drawing, a configuration or a structure equivalent to that in the sample analysis element 11 described above is denoted by the same reference numeral and description thereof is omitted.

A plurality of first long pieces 17a is disposed between the metallic nano-projection groups 16a which are divided in the first direction DR. That is, the first long pieces 17a are disposed at the long pitch LP in the first direction DR. The first long pieces 17a extend parallel in the second direction SD. Each first long piece 17a can linearly extend. Each first long piece 17a can continuously extend from an edge to an edge of the contour of the dielectric film 14.

A plurality of second long pieces 17b (only one is shown) is disposed between the metallic nano-projection groups 16a which are divided in the second direction SD. That is, the second long pieces 17b are disposed at the long pitch LP in the second direction SD. The second long pieces 17b extend parallel in the first direction DR. Each second long piece 17b can linearly extend. Each second long piece 17b can continuously extend from an edge to an edge of the contour of the dielectric film 14. In this way, the first long pieces 17a and the second long pieces 17b form a frame that continuously surrounds the metallic nano-projection group 16a for each metallic nano-projection group 16a. That is, the first long pieces 17a and the second long pieces 17b extend in a lattice form on the surface of the dielectric film 14.

In the sample analysis element 11a, if incident light that is circularly-polarized light is irradiated, the propagating surface plasmon resonance based on an evanescent wave occurs according to the setting of the long pitch LP in the x-axis direction and the y-axis direction. The propagating surface plasmon resonance is combined with the localized surface plasmon resonance of the metallic nano-projection 15. A so-called hybrid mode is established. In this way, the localized surface plasmon resonance is enhanced by the propagating surface plasmon resonance, and thus, near-field light is intensified on the surface of the metallic nano-projection 15. A so-called hot spot is formed. In addition, since in each metallic nano-projection group 16a, the gap between the metallic nano-projections 15 is set to be the short pitch SP smaller than the long pitch LP, compared to a case where the gap between the metallic nano-projections 15 is set to be the long pitch LP, the surface density of the metallic nano-projection 15 is increased. The surface density of the hot spot is increased. In addition, in a case where the sample analysis element 11a is incorporated into the detecting device 31, it is favorable if the light source 36 emits light that is circularly-polarized light.

Figure 12:
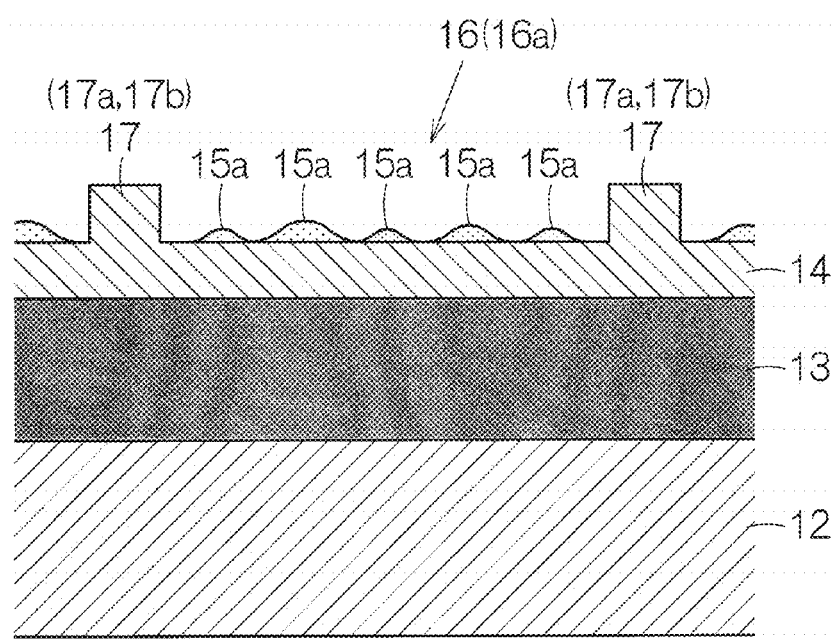
FIG. 12 is a vertical cross-sectional view showing a sample analysis element according to another modification example.

In addition, for example, as shown in FIG. 12, in a single metallic nano-projection group 16 or 16a, so-called island-shaped metallic nanoparticles 15a may also be disposed in a random manner. Even in such a case, the long pitch LP of the long piece 17, 17a, or 17b can be maintained. Therefore, the long pitch LP of the metallic nano-projection group 16 or 16a can also be maintained. In the same manner as described above, the hybrid mode can be established. The surface density of the hot spot can be increased. The island-shaped metallic nanoparticle 15a can be formed based on aggregation of metal materials in thin-film formation by sputtering.

In addition, this embodiment has been described in detail, as described above. However, it will be easily understood by those skilled in the art that many modifications are possible which do not substantively depart from the new matters and the advantageous effects of the invention. Therefore, all of such modification examples are included in the scope of the invention. For example, the term stated at least once along with a different term in a broader sense or the same meaning in the specification or the drawings can be replaced with a different term in anyplace of the specification or the drawings. Further, the configurations and the operations of the sample analysis element, the detecting device, and the like are also not limited to those described in the embodiment and various modifications are possible.

The entire disclosure of Japanese Patent Application No. 2012-008162 filed Jan. 18, 2012 is expressly incorporated by reference herein.

What is claimed is:

1. A sample analysis element comprising:
a substrate;
a metal film is formed on the surface of the substrate;
a dielectric film is formed on the surface of the metal film;
a plurality of metallic nano-body groups; and
a long piece formed on the dielectric film between the plurality of metallic nano-body groups adjacent to each other,
wherein the plurality of metallic nano-body groups includes metallic nano-bodies that are dispersed on the dielectric surface,
the metallic nano-body is smaller than the wavelength of incident light,
the plurality of metallic nano-body groups is arranged in one direction or a plurality of directions at a pitch that resonates with the incident light, and
the long piece is formed of a material having no free electron that performs resonance oscillation with the incident light.

2. The sample analysis element according to claim 1, wherein the height of the long piece is higher than the height of the metallic nano-body.

3. The sample analysis element according to claim 1, wherein the metallic nano-body groups are arranged in one direction at the pitch that resonates with the incident light, and also arranged in a direction intersecting one direction at the pitch that resonates with the incident light, and the long piece is formed on the dielectric surface between the plurality of metallic nano-body groups adjacent to each other.

4. The sample analysis element according to claim 1, wherein the metallic nano-body is an island-shaped metallic nanoparticle.

5. A detecting device comprising:
a sample analysis element in which a substrate, a metal film is formed on the surface of the substrate, a dielectric film is formed on the surface of the metal film, and a plurality of metallic nano-body groups is arranged;
a light source that emits light toward the metallic nano-body group; and
a photodetector that detects the light that is emitted from the metallic nano-body group according to the irradiation of the light,
wherein the sample analysis element includes a dielectric surface, and a long piece formed on the dielectric surface between the plurality of metallic nano-body groups adjacent to each other,
the plurality of metallic nano-body groups includes metallic nano-bodies that are dispersed on the dielectric surface,
the metallic nano-body is smaller than the wavelength of incident light, the plurality of metallic nano-body groups are arranged in one direction or a plurality of directions at a pitch that resonates with the incident light, and the long piece is formed of a material having no free electron that performs resonance oscillation with the incident light.

6. The detecting device according to claim 5, wherein the height of the long piece is higher than the height of the metallic nano-body.

7. The detecting device according to claim 5, wherein the metallic nano-body groups are arranged in one direction at the pitch that resonates with the incident light, and also arranged in a direction intersecting one direction at the pitch that resonates with the incident light, and the long piece is formed on the dielectric surface between the plurality of metallic nano-body groups adjacent to each other.

8. The detecting device according to claim 5, wherein the metallic nano-body is an island-shaped metallic nanoparticle.

\* \* \* \* \*